(12) United States Patent
Lemay et al.

(10) Patent No.: US 8,337,478 B2
(45) Date of Patent: Dec. 25, 2012

(54) ERGONOMIC TAMPON APPLICATOR

(75) Inventors: Jessica E. Lemay, Paramus, NJ (US);
Kathryn G. Bennett, Fairfield, CT (US);
Keith J. Edgett, Ramsey, NJ (US); Dane R. Jackson, Bloomingdale, NJ (US);
Mario A. Turchi, Tenafly, NJ (US);
Susanne Weber, New York, NY (US)

(73) Assignee: Playtex Products, Inc., Westport, CT (US)

( * ) Notice: Subject to any disclaimer, the term of this patent is extended or adjusted under 35 U.S.C. 154(b) by 74 days.

(21) Appl. No.: 12/798,990

(22) Filed: Apr. 15, 2010

(65) Prior Publication Data
US 2010/0204636 A1 Aug. 12, 2010

Related U.S. Application Data

(63) Continuation of application No. 10/242,474, filed on Sep. 12, 2002, now Pat. No. 7,727,208.

(51) Int. Cl.
*A61F 13/20* (2006.01)
*A61F 13/15* (2006.01)

(52) U.S. Cl. ............. 604/385.17; 604/385.18; 604/904; 604/11; 604/12; 604/13; 604/14

(58) Field of Classification Search ............. 604/385.17, 604/385.18, 904, 11, 12, 13, 14
See application file for complete search history.

(56) References Cited

U.S. PATENT DOCUMENTS

| | | | |
|---|---|---|---|
| 615,425 A | 12/1898 | Butler | |
| 652,848 A | 7/1900 | Hill | |
| 747,444 A | 12/1903 | La Veine | |
| 1,191,736 A | 7/1916 | Robertson | |
| D67,464 S | 6/1925 | Johnson | |
| 1,554,690 A | 9/1925 | Pride | |
| 1,737,454 A | 11/1929 | Foley | |
| D111,212 S | 9/1938 | Meyer | |
| 2,476,956 A | 7/1949 | Bonham | 604/15 |
| 2,489,502 A | 11/1949 | Ruth | 604/18 |
| 2,587,717 A | 3/1952 | Fourness | 604/18 |
| 2,877,767 A | 3/1959 | Kramer | |
| 2,923,295 A | 2/1960 | Guerriero | |

(Continued)

FOREIGN PATENT DOCUMENTS

EP 0418791 3/1991

(Continued)

OTHER PUBLICATIONS

International Search Report from corresponding PCT Application No. PCT/US03/28181 dated May 11, 2004.

(Continued)

*Primary Examiner* — Jacqueline F. Stephens
(74) *Attorney, Agent, or Firm* — Olhandt, Greeley, Ruggiero & Perle, L.L.P.

(57) ABSTRACT

A tampon applicator barrel includes a wall forming a tube with a center axis therthrough and with a hollow interior volume. The tube has a first barrel end and a second barrel end opposite the first barrel end to form a length therebetween that corresponds to the length of the center axis. The tube increases in diameter along the length of the tube from a first diameter to a second diameter that forms a main body section, and decreases in diameter along the length of the tube from the second diameter to a third diameter that forms a reverse taper section. The center axis is substantially straight throughout the extant of the tube.

18 Claims, 2 Drawing Sheets

U.S. PATENT DOCUMENTS

| | | | |
|---|---|---|---|
| D197,751 S | 3/1964 | Rigney et al. | |
| 3,139,886 A | 7/1964 | Tallman et al. | 604/12 |
| 3,572,335 A | 3/1971 | Robinson | |
| 3,575,169 A | 4/1971 | Voss et al. | 604/18 |
| 3,628,533 A | 12/1971 | Loyer | 128/263 |
| 3,765,416 A | 10/1973 | Werner et al. | 128/263 |
| 4,048,998 A | 9/1977 | Nigro | 604/14 |
| D250,663 S | 12/1978 | Koch et al. | D24/99 |
| 4,198,978 A | 4/1980 | Nigro | 128/285 |
| D265,576 S | 7/1982 | Lamkin et al. | |
| 4,361,150 A | 11/1982 | Voss | 604/15 |
| 4,398,532 A | 8/1983 | Sweeney, III | |
| 4,421,504 A | 12/1983 | Kline | 604/12 |
| 4,428,370 A | 1/1984 | Keely | 128/838 |
| 4,508,531 A | 4/1985 | Whitehead | 604/14 |
| D279,504 S | 7/1985 | Tump | |
| 4,536,178 A | 8/1985 | Lichstein et al. | 604/15 |
| D287,876 S | 1/1987 | Blatherwick et al. | |
| 4,676,773 A | 6/1987 | Sheldon | 604/16 |
| D301,378 S | 5/1989 | Shippert | |
| 4,846,802 A | 7/1989 | Sanders, III | 604/15 |
| 4,857,044 A | 8/1989 | Lennon | |
| 4,891,042 A | 1/1990 | Melvin et al. | 604/18 |
| 4,900,299 A | 2/1990 | Webb | |
| 4,921,474 A | 5/1990 | Suzuki et al. | 604/16 |
| 5,080,659 A | 1/1992 | Nakanishi | 604/904 |
| 5,158,535 A | 10/1992 | Paul et al. | 604/15 |
| 5,290,501 A | 3/1994 | Klesius | 264/322 |
| 5,295,952 A | 3/1994 | Pietrafitta | |
| 5,395,309 A | 3/1995 | Tanaka et al. | |
| 5,453,085 A | 9/1995 | Schoelling | 604/15 |
| D384,417 S | 9/1997 | Zurbay | |
| 5,788,663 A | 8/1998 | Igaue et al. | 604/15 |
| 5,873,971 A | 2/1999 | Balzar | |
| D415,565 S | 10/1999 | Hayes et al. | D24/141 |
| 6,045,526 A | 4/2000 | Jackson | 604/15 |
| 6,248,089 B1 | 6/2001 | Porat | 604/17 |
| 6,264,626 B1 | 7/2001 | Linares et al. | 604/15 |
| 6,302,861 B2 | 10/2001 | Tweddell, III et al. | |
| 6,364,854 B1 | 4/2002 | Ferrer et al. | 604/60 |
| 6,368,442 B1 | 4/2002 | Linares et al. | 156/198 |
| 6,416,488 B1 | 7/2002 | Jackson et al. | |
| 6,423,025 B1 | 7/2002 | Buzot | 604/15 |
| 6,432,075 B1 | 8/2002 | Wada et al. | 604/15 |
| 6,432,076 B1 | 8/2002 | Wada et al. | 604/15 |
| 6,450,986 B1 | 9/2002 | Binner | 604/15 |
| 6,478,764 B1 | 11/2002 | Suga | 604/15 |
| 6,511,452 B1 | 1/2003 | Rejai et al. | |
| 6,572,577 B1 | 6/2003 | Binner et al. | 604/15 |
| 6,610,025 B2 | 8/2003 | Berg et al. | 604/14 |
| D480,650 S | 10/2003 | Moore et al. | |
| 6,648,846 B2 | 11/2003 | Binner et al. | 604/15 |
| 6,673,032 B2 | 1/2004 | Buzot | 604/15 |
| 6,685,787 B2 | 2/2004 | Linares et al. | 156/198 |
| 6,685,788 B2 | 2/2004 | Linares et al. | 156/203 |
| D492,033 S | 6/2004 | Jarmon et al. | |
| 6,786,883 B2 | 9/2004 | Shippert | |
| D509,746 S | 9/2005 | Mero et al. | |
| D515,212 S | 2/2006 | Edgett et al. | |
| 7,081,110 B2 | 7/2006 | Karapasha | |
| 7,172,573 B1 | 2/2007 | Lamb | 604/59 |
| 7,704,242 B2 | 4/2010 | LeMay et al. | |
| 7,727,208 B2 | 6/2010 | Lemay | |
| 2002/0107088 A1 | 8/2002 | Lamkin et al. | |
| 2002/0143287 A1 | 10/2002 | Buzot | 604/14 |
| 2002/0151859 A1 | 10/2002 | Schoelling | |
| 2003/0028176 A1 | 2/2003 | Berg et al. | 604/385.18 |
| 2003/0028177 A1 | 2/2003 | Berg et al. | 604/385.18 |
| 2003/0040695 A1 | 2/2003 | Zhao et al. | |
| 2003/0073947 A1 | 4/2003 | Binner et al. | 604/15 |
| 2003/0073948 A1 | 4/2003 | Binner et al. | 604/15 |
| 2003/0105421 A1 | 6/2003 | Jarmon et al. | |
| 2003/0216680 A1 | 11/2003 | Binner et al. | 604/15 |
| 2003/0236485 A1 | 12/2003 | Fedyk et al. | 604/11 |
| 2004/0199102 A1 | 10/2004 | LeMay et al. | |

FOREIGN PATENT DOCUMENTS

| | | |
|---|---|---|
| EP | 1 101 472 | 2/2005 |
| EP | 1 040 808 | 3/2005 |
| EP | 1 101 473 | 8/2009 |
| JP | 59-111756 | 6/1984 |
| JP | 03-106365 | 5/1991 |
| JP | 04322647 | 11/1992 |
| JP | 04322648 | 11/1992 |
| JP | 06-086789 | 3/1994 |
| JP | 2000-279446 | 10/2000 |
| JP | 2001-145657 | 5/2001 |
| JP | 2003153947 | 5/2003 |
| JP | 2003180742 | 7/2003 |
| JP | 2003310660 | 11/2003 |
| WO | 00-66213 | 11/2000 |

OTHER PUBLICATIONS

U.S. Appl. No. 10/619,892, filed Jul. 2003, Lemay et al.
U.S. Appl. No. 10/619,677, filed Jul. 2003, Lemay et al.
Supplementary European Search Report dated Jul. 28, 2010 from corresponding European Application No. 03754471.5.
European Examination Report dated Feb. 4, 2011 from corresponding European Application No. 03 754 471.5.
Canadian Examination Report Dated Oct. 7, 2009 From Corresponding Application No. 2,498,508.
Canadian Examination Report Dated Dec. 18, 2008 From Corresponding Application No. 2,498,508.
Canadian Examination Report Dated Jan. 15, 2008 From Corresponding Application No. 2,498,508.
Canadian Examination Report Dated May 3, 2007 From Corresponding Application No. 2,498,508.
Notice of Reasons for Rejection Dated Aug. 5, 2008 From Corresponding Japanese Application No. 2004-536364.
Final Notice of Rejection Dated May 12, 2009 From Corresponding Japanese Application No. 2004-536364.
Notice of Reasons for Rejection Dated Jan. 11, 2005 From Corresponding Japanese Application No. 2004-027399.
Official Action Dated Apr. 26, 2005 From Corresponding Japanese Application No. 2004-27406.
Notice of Reasons for Rejection Dated Oct. 4, 2011 From Corresponding Japanese Application No. 2009-209408.
Official Action Received Jul. 2, 2010 From Corresponding Mexican Application No. PA/a/2005/002767.
Official Action Received Nov. 26, 2010 From Corresponding Mexican Application No. PA/a/2005/002767.
Official Action Received Feb. 16, 2011 From Corresponding Mexican Application No. PA/a/2005/002767.
US Office Action Dated Jun. 26, 2007 From Corresponding U.S. Appl. No. 29/205,148.
US Office Action Dated Jun. 3, 2005 From Corresponding U.S. Appl. No. 29/205,148.
US Office Action Dated May 16, 2005 From Corresponding U.S. Appl. No. 29/201,235.
US Office Action Dated Oct. 1, 2007 From Corresponding U.S. Appl. No. 29/201,242.
US Office Action Dated Aug. 25, 2005 From Corresponding U.S. Appl. No. 29/201,242.
US Office Action Dated Jul. 2, 2007 From Corresponding U.S. Appl. No. 29/201,242.
US Office Action Dated Jun. 9, 2009 From Corresponding U.S. Appl. No. 10/242,474.
US Office Action Dated Dec. 16, 2008 From Corresponding U.S. Appl. No. 10/242,474.
US Office Action Dated May 5, 2008 From Corresponding U.S. Appl. No. 10/242,474.
US Office Action Dated Dec. 20, 2006 From Corresponding U.S. Appl. No. 10/242,474.
US Office Action Dated Jun. 16, 2006 From Corresponding U.S. Appl. No. 10/242,474.
US Office Action Dated May 20, 2004 From Corresponding U.S. Appl. No. 10/242,474.

US Office Action Dated Jan. 12, 2004 From Corresponding U.S. Appl. No. 10/242,474.
US Office Action Dated Mar. 10, 2005 From Corresponding U.S. Appl. No. 10/242,474.
US Office Action Dated Feb. 8, 2005 From Corresponding U.S. Appl. No. 10/242,474.
US Office Action Dated Nov. 17, 2004 From Corresponding U.S. Appl. No. 10/242,474.
US Office Action Dated Dec. 30, 2005 From Corresponding U.S. Appl. No. 10/242,474.
US Office Action Dated Nov. 21, 2005 From Corresponding U.S. Appl. No. 10/242,474.
US Office Action Dated Aug. 11, 2005 From Corresponding U.S. Appl. No. 10/242,474.
US Office Action Dated May 16, 2005 From Corresponding U.S. Appl. No. 29/201,216.

ERGONOMIC TAMPON APPLICATOR

RELATED APPLICATION

This application is a continuation of prior U.S. application Ser. No. 10/242,474, filed Sep. 12, 2002 now U.S. Pat. 7,727,208. U.S. application Ser. No. 10/242,474, filed Sep. 12, 2002, is incorporated by reference herein in its entirety.

BACKGROUND

1. Field of the Invention

The present disclosure relates generally to an improved tampon or tampon applicator. More particularly, the present disclosure relates to a tampon applicator with a barrel that has a reverse taper section for improved ease of use and user comfort.

2. Description of the Prior Art

Commercial tampon applicators typically consist of a barrel and a plunger used to expel an absorbent pledget housed in the barrel. The barrel is typically sub-divided into three sections, namely a finger grip, an insertion tip, and a main body section, which is located between the finger grip and insertion tip sections.

The finger grip section is typically the same diameter as the main body section of the barrel, but some designs (e.g., Playtex® Gentle Glide®) have a reduced diameter grip for improve grippability. The main body section is typically linear, except on plastic molded barrels where there is a slight taper to improve release characteristics from the manufacturing mold. The insertion tip section on some types of barrels have "petals" which curve over and enclose the pledget (i.e., rounded tip) housed in the barrel, but readily flex outwardly as the pledget is expelled through the insertion tip.

SUMMARY

The present disclosure provides a tampon applicator that is ergonomic.

The present disclosure also provides such an ergonomic tampon applicator with a plunger and a barrel.

The present disclosure further provides such an ergonomic tampon applicator barrel having a finger grip section, a reverse taper section, a main body section and an insertion tip section.

The present disclosure still further provides such an ergonomic tampon applicator barrel reverse taper section where the reverse taper is towards the finger grip section.

The present disclosure also provides such an ergonomic tampon applicator barrel finger grip section having a finger accepting region.

The present disclosure further provides such an ergonomic tampon applicator insertion tip section formed with a plurality of petals.

The present disclosure still further provides such an ergonomic tampon applicator main body section with a maximum diameter section that is sensually perceivable to a user to alert the user to the proper insertion depth of the applicator.

The present disclosure also provides such an ergonomic tampon applicator having a plunger with at least one flared end.

These and other objects and advantages of the present disclosure will be appreciated from an ergonomically improved tampon applicator having a plunger and a barrel, of the present disclosure. The barrel has four distinct sections, namely a finger grip section, a reverse taper section, a main body section, and an insertion tip section. The reverse taper section is tapered towards the fingergrip section, and the main body section is tapered in an opposite direction towards the insertion tip section. A maximum diameter is formed where the reverse taper section and main body section meet on the barrel. The maximum diameter provides a sensory indicator to the user to alert the user when the applicator has been inserted to the proper depth in the vagina.

DETAILED DESCRIPTION

Figure 1:
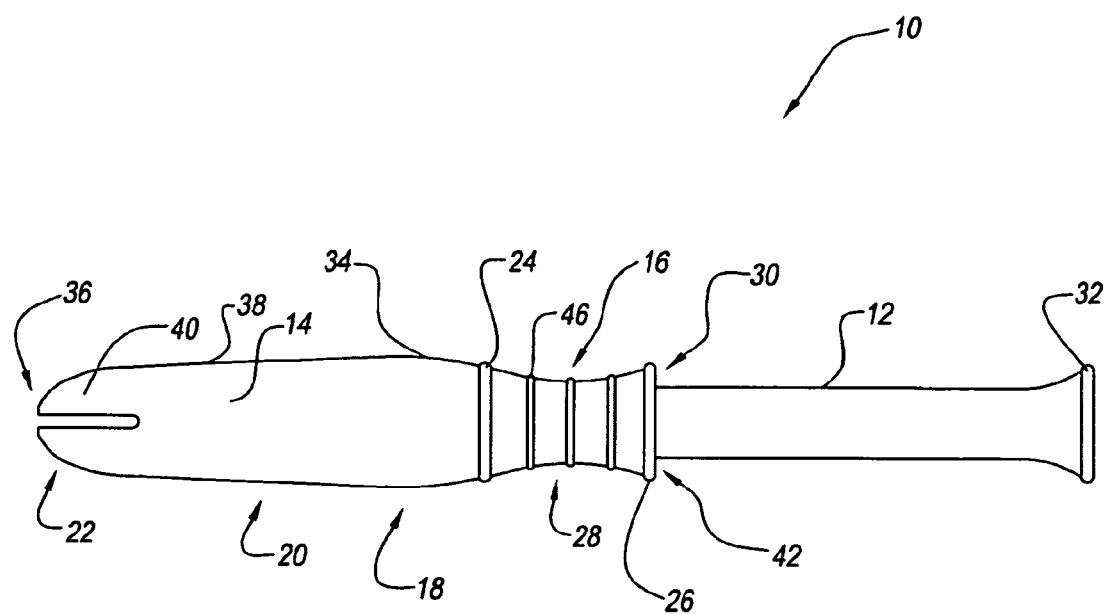
FIG. 1 is a plan view of a tampon applicator of the present disclosure.

Referring to drawings and, in particular, FIG. 1, there is shown an ergonomically improved tampon applicator according to the present disclosure generally represented by reference numeral 10. The ergonomically improved applicator 10 is easier to use and more comfortable to insert and remove. Applicator 10 includes a plunger 12 and a barrel 14.

Barrel 14 may be divided into four sections, as opposed to three sections typically found in prior art tampon applicators. The four sections include a finger grip section 16, a reverse taper section 18, a main body section 20, and an insertion tip section 22.

Finger grip section 16 is bound by a forward edge ridge 24 and a rearward edge ridge 26. Forward edge ridge 24 provides a firm grip surface during insertion of applicator 10 into the vaginal vault. Rearward edge ridge 26 provides a firm grip surface during expulsion of the pledget (not shown) and during removal of applicator 10 from the body. Forward and rearward edge ridges 24, 26 are about 6 mm to about 22 mm in diameter. Preferably, the forward and rearward edges 24, 26 are about 11 mm to about 17 mm in diameter, with about 14 mm being the most preferred diameter.

A finger accepting region 28 is formed between forward edge ridge 24 and rearward edge ridge 26. To ensure an adequate area to accept a user's finger or fingers, forward edge ridge 24 and rearward edge ridge 26 are spaced about 13 mm to about 40 mm apart. More preferably, forward edge ridge 24 and rearward edge ridge 26 are spaced about 17 mm to about 21 mm apart, with about 19 mm being the most preferred spacing. Finger accepting region 28 may be concave, convex, flat, or any combinations thereof. Preferably, region 28 is concave, which conforms to the contour of a user's finger. The maximum diameter of region 28 is preferably slightly less than the diameter of edge ridges 24, 26. Preferably, region 28 has a maximum to minimum diameter ratio of about 1.10 to about 1.75, with a more preferred ratio of about 1.25 to about 1.35.

Finger accepting region 28 may also include one or more gripping structures 46 to improve grippability of applicator 10. Suitable gripping structures 46 include, for example, one or more and preferably two or more, embossments, protuberances, slits, grooves, louvers, perforations, lances, abrasive medias, high wet coefficient of friction materials, pressure sensitive adhesives, or any combinations thereof. In addition, gripping structures 46 may be formed in any shape, including, for example, arc, circle, concave, cone, convex, diamond, line, oval, polygon, rectangle, rib, square, triangle, or any combinations thereof.

The maximum diameter 34 of applicator barrel 14 occurs at the forward end of reverse taper section 18. Reverse taper is meant to include a taper in the reverse direction, i.e. in a direction away from the insertion end of applicator 10, but not necessarily the same dimensional taper as main body section 20. The diameter of reverse taper section 18 tapers down toward forward edge ridge 24, where the diameter is equal to or slightly less than the diameter of forward edge ridge 24. This taper may be linear or curvilinear.

Maximum diameter 34 of barrel 14 exerts a slightly greater pressure than the smaller diameter portions of the barrel on the vaginal opening. This unique feature of barrel 14 provides a sensually perceivable way of signaling or indicating to a user that applicator 10 has been inserted to the correct depth in the vagina. Thus, the location of maximum diameter 34 along the length of barrel 14 is a critical aspect of the present disclosure. The location of maximum diameter 34 on barrel 14 is about 32 mm to about 54 mm in the axial direction of barrel 14 from forward end 36 of insertion tip 22. Preferably maximum diameter 34 is located about 40 mm to about 50 mm, and more preferably about 44 mm in the axial direction of barrel 14 from forward end 36 of insertion tip 22.

Main body section 20 is joined to reverse taper section 18 where maximum diameter 34 of barrel 14 is located. Main body section 20 tapers toward insertion tip section 22 in either a linear or curvilinear fashion so that its smallest diameter occurs where main body section 20 meets insertion tip section 22. The ratio of maximum diameter 34 to the diameter at the forward end 38 of main body section 20 is about 1.1 to about 1.5, and more preferably about 1.2 to about 1.3. This tapering of main body section 20 facilitates insertion comfort by gradually parting the vulva-vaginal channel over a longer length than that of only insertion tip section 22.

Insertion tip section 22 begins where there is a substantial change in the curvature of the forward portion of the barrel that is where the pledget-enclosing petals 40 are formed. In applicator designs where no petals are used, insertion tip 22 is the forward edge of the main body section 20 of barrel 14. The preferred insertion tip 22 is the petal type with a curvature that approximates an elliptical or hyperbolic curve. Preferably, insertion tip 22 has about 2 to about 12 petals, and more preferably about 3 to about 8 petals. The ratio of the maximum diameter of insertion tip section 22, which occurs at the plane where its rearward edge meets forward end 38 of main body section 20, to the total axial length of the insertion tip section along a horizontal axis of applicator 10, is about 0.9 to about 1.8, and more preferably about 1.1 to about 1.3.

The less severe curvature of insertion tip section 22 also facilitates insertion comfort by gradually parting the vulva-vaginal channel along its longer length.

It should be understood that while tampon applicator barrel 14 of the present disclosure is depicted as having four sections, namely a finger grip section, a reverse taper section, a main body section, and an insertion tip section, the tampon applicator barrel can include a reverse taper section and at least one additional section selected from a finger grip section, a main body section, an insertion tip section, or any combinations thereof.

The interior wall of barrel 14 that houses the pledget may have the same basic sidewall shape as its exterior wall. However, molding such a complicated interior wall requires a complex manufacturing process. Alternately, the interior wall can be practically straight walled (a slight taper may be required for tooling release) while the exterior wall has the sectional shapes discussed before, thus simplifying the molding process.

Figure 2:
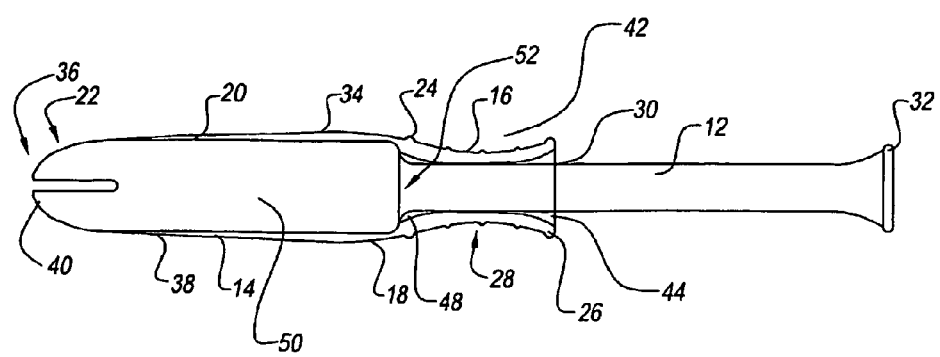
FIG. 2 is a cut away view of the tampon applicator of FIG. 1 depicting an absorbent pledget housed in the barrel.
Figure 3:
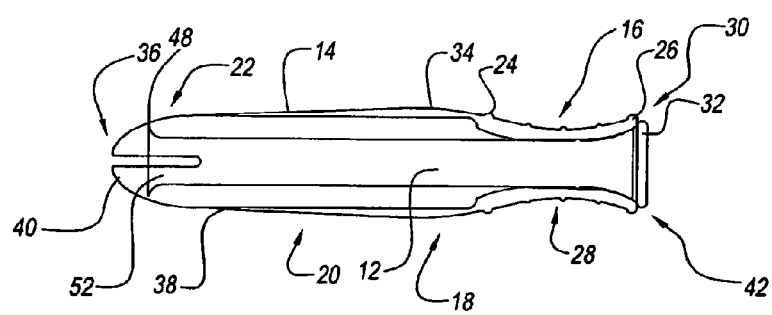
FIG. 3 is a cut away view of the tampon applicator of FIG. 2 after the pledget has been expelled from the barrel.

Referring to FIGS. 2 and 3, barrel 14 has a finger grip end 42. Plunger 12 telescopically fits into the finger grip end 42 of barrel 14. Plunger 12 has a diameter slightly smaller than the smallest diameter of finger receiving region 28 so that plunger 12 telescopically fits throughout the interior of barrel 14. Preferably, in one embodiment of the present disclosure, plunger 12 has a diameter about 4 mm to about 18 mm. More preferably, plunger 12 has a diameter about 5 mm to about 9 mm with the most preferred diameter being about 7 mm.

Plunger 12 has a first flare 32 at its distal end and a second flare or retaining structure 48 at its opposite barrel end 52. Finger grip section 16 has a plunger receiving end 30. Plunger receiving end 30 of finger grip section 16 has a chamfer 44 to receive first flare 32 of plunger 12 during pledget expulsion. This permits shortening the length of the section of plunger 12 that protrudes from barrel 14 since all of the protruded length is available for the telescopic action. This in turns results in a more ergonomic applicator. Such an ergonomic applicator is conducive to one handed use, since the distance between finger grip section 16 and first flare 32, where the fingertip is placed, is reduced by an amount equal to the length of first flare 32. Second flare or retaining feature 48 on barrel end 52 of plunger 12 prevents separation from barrel 14.

First flare 32 has a maximum diameter about 6 mm to about 22 mm. Preferably the maximum diameter is about 12 mm to about 16 mm, with about 13 mm being the most preferred maximum diameter, in order to provide a secure area for a user's fingertip during pledget expulsion. The rearward end of first flare 32 may be flat, concave, or convex. Preferably, it is concave to provide a secure area for the fingertip.

Second flare 48 has a maximum diameter about 5 mm to about 20 mm. Preferably the maximum diameter is about 11 mm to about 14 mm, with about 13 mm being the most preferred maximum diameter, in order to prevent separation from barrel 14.

Although it might be implied that the cross-sectional shape of plunger 12 and barrel 14 is circular, due to the use of the term 'diameter', it should be understood that the cross-sectional shape can be non-circular, such as oval or polygonal. Furthermore, the cross-sectional shape can vary along the length of both plunger 12 and barrel 14. For example, a circular plunger with a polygonal finger grip and an oval main body may be formed.

The pledget housed by applicator barrel 14 preferably has a tapered forward end that corresponds to that of insertion tip 22. The matching taper supports petals 40 during insertion of applicator 10 so that the petals cannot flex out of shape, thus enhancing comfort. Additionally, during expulsion from applicator 10, the pledget's tapered tip will gradually part the vaginal channel, further enhancing user comfort.

Suitable materials for forming plunger 12 and/or barrel 14 include, for example, biopolymer, cardboard, heat shrink plastic, paper slurry, plastic, plastic tubing, pulp slurry, pulp-molded paper, or any combinations thereof.

To reduce friction and/or increase strength, plunger 12 and/or barrel 14 may be coated with a coating material. Suitable coating materials include, for example, cellophane, cellulose, epoxy, lacquer, nitrocellulose, nylon, plastic, polyester, polylactide, polyolefin, polyvinyl alcohol, polyvinyl chloride, silicone, wax, or any combinations thereof.

The foregoing specification and drawings are merely illustrative of the present invention and are not intended to limit the invention to the disclosed embodiments. Variations and changes, which are obvious to one skilled in the art, are intended to be within the scope and nature of the present invention, which is defined in the appended claims.

What is claimed is:

1. A tampon applicator barrel comprising:
a wall forming a tube with a center axis therthrough and with a hollow interior volume, the tube having a first barrel end and a second barrel end opposite the first barrel end that is a free end, the first barrel end and the second barrel end form a length therebetween that corresponds to the length of the center axis, the tube increasing in diameter along the length of the tube from a first diameter to a second diameter that forms a main body section, and decreasing in diameter along the length of the tube from the second diameter to a third diameter that forms a reverse taper section, wherein the center axis is substantially straight throughout the extant of the tube.

2. The tampon applicator barrel of claim 1, wherein the third diameter connects directly to a finger grip section.

3. The tampon applicator barrel of claim 2, wherein the finger grip section has a length from the third diameter to a fourth diameter, and wherein the tube decreases in diameter from the third diameter to the fourth diameter.

4. The tampon applicator barrel of claim 3, wherein the tube increases in diameter along the length of the tube from the fourth diameter to a fifth diameter.

5. The tampon applicator barrel of claim 4, wherein the fifth diameter is at the second barrel end.

6. The tampon applicator barrel of claim 5, wherein the second barrel end has an opening into the interior volume for receipt of a plunger that forms an applicator assembly.

7. The applicator assembly of claim 6, wherein the plunger has a first plunger end and a second plunger end, and wherein the first plunger end is within the interior volume and the second plunger end has a shape that is complimentary to the shape of the finger grip section between the fourth diameter and the fifth diameter.

8. The tampon applicator barrel of claim 2, wherein the finger grip section has a forward edge ridge adjacent the reverse taper section.

9. The tampon applicator barrel of claim 2, wherein the finger grip section has a rearward edge ridge at the second barrel end.

10. The tampon applicator barrel of claim 2, wherein the finger grip section has at least one gripping structure thereon.

11. The tampon applicator barrel of claim 2, wherein the finger grip section has a forward edge ridge adjacent the reverse taper section, wherein the finger grip section has a rearward edge ridge at the second barrel end, and wherein the forward edge ridge and the rearward edge ridge has a finger accepting region therebetween.

12. The tampon applicator barrel of claim 1, wherein the first diameter is connected to an insertion tip section.

13. The tampon applicator barrel of claim 12, wherein the diameter of the tube decreases in diameter along the length of the tube from the first diameter to the first barrel end in the insertion tip section.

14. The tampon applicator barrel of claim 1, wherein the insertion tip section has a plurality of petals formed by separations in the tube.

15. The tampon applicator barrel of claim 1, wherein the second diameter is a maximum diameter of the tube.

16. The tampon applicator barrel of claim 1, wherein the reverse taper section is shorter than the main body section along the length of the tube.

17. The tampon applicator barrel of claim 1, wherein the tube has an interior wall that houses a pledget opposite an exterior wall, and wherein the interior wall has the same shape as the exterior wall.

18. The tampon applicator barrel of claim 1, wherein the tube has an interior wall that houses a pledget opposite an exterior wall, and wherein the interior wall is substantially straight walled.

* * * * *